United States Patent
Simmons et al.

(10) Patent No.: US 9,579,410 B2
(45) Date of Patent: Feb. 28, 2017

(54) SELF-POWERED FOOTWEAR, SANITIZING SYSTEM

(71) Applicants: Corinne K. Simmons, Yakima, WA (US); James A. Brunner, Yakima, WA (US)

(72) Inventors: Corinne K. Simmons, Yakima, WA (US); James A. Brunner, Yakima, WA (US)

( * ) Notice: Subject to any disclaimer, the term of this patent is extended or adjusted under 35 U.S.C. 154(b) by 0 days.

(21) Appl. No.: 14/732,376

(22) Filed: Jun. 5, 2015

(65) Prior Publication Data
US 2016/0354502 A1   Dec. 8, 2016

(51) Int. Cl.
*A61L 2/10*   (2006.01)
*A61L 2/24*   (2006.01)

(52) U.S. Cl.
CPC ..................................... *A61L 2/10* (2013.01)

(58) Field of Classification Search
CPC . A61L 2/10; A61L 2/0047; A61L 2/24; A61L 2/18; A61L 2/28; A61L 2/14; A61L 2/202; A61L 2/26
USPC ...... 422/24, 196.3; 250/504 R, 492.1, 336.1, 250/365, 394, 453.11, 454.11, 494.1; 310/319, 339
See application file for complete search history.

(56) References Cited

U.S. PATENT DOCUMENTS

| | | | | |
|---|---|---|---|---|
| 7,875,869 B1* | 1/2011 | Shadan | ................. | A61L 2/0047 250/365 |
| 8,277,741 B2* | 10/2012 | McCabe | ................... | A61L 2/10 422/105 |
| 8,427,034 B2* | 4/2013 | King | ...................... | E04F 15/02 310/339 |
| 8,470,239 B1* | 6/2013 | Kerr | .......................... | A61L 2/10 422/22 |
| 8,512,631 B2* | 8/2013 | Kerr | .......................... | A61L 2/10 422/22 |
| 8,617,464 B2* | 12/2013 | Kerr | ...................... | A61L 2/0047 422/22 |
| 8,624,202 B2* | 1/2014 | Gil | ............................ | A61L 2/10 250/453.11 |
| 8,631,533 B1* | 1/2014 | Gulian | ...................... | A61L 2/10 15/36 |
| 9,198,991 B2* | 12/2015 | Dombrowsky | ........... | A61L 2/10 |
| 9,211,352 B2* | 12/2015 | Kassel | ...................... | A61L 2/10 |
| 9,272,058 B1* | 3/2016 | Montgomery | ........ | A61L 2/0047 |
| 2010/0193709 A1* | 8/2010 | Dalton | ..................... | A61L 2/10 250/504 R |
| 2012/0167325 A1* | 7/2012 | Omidi | ................... | A47L 23/263 15/210.1 |
| 2013/0154441 A1* | 6/2013 | Redmond | ................ | G08G 1/02 310/319 |
| 2014/0299783 A1* | 10/2014 | Valentino | .............. | G01J 1/0488 250/394 |

\* cited by examiner

*Primary Examiner* — David A Vanore

(57) ABSTRACT

The present invention relates to a self-powered, footwear sanitizing system configured to substantially neutralize biological contaminants on the soles of shoes when a wearer of the shoes steps onto the system, the system has a method to generate sanitizing radiation of 254 nm (UVC), a means for delivering sanitizing radiation from the mat to the underside of a wearer's shoes and a piezo-electric or mechano-luminescence generator to power the system.

2 Claims, 4 Drawing Sheets

SELF-POWERED FOOTWEAR, SANITIZING SYSTEM

BACKGROUND

The embodiments herein relate generally to floor mats. More specifically, embodiments of the invention are directed at a self-powered footwear sanitizing system that substantially neutralizes biological contaminants on the soles of the user's footwear.

A standard of today's society is covering our feet for comfort and protection from items that can cause potential foot injury. The constant use of footwear has also resulted in the footwear coming into contact with biological contaminants found on any public or private area where walking occurs. These biological contaminants are then spread to other locations including the home, schools, stores, etc. which can ultimately infect someone else.

To address the issue of the spread of biological contaminants from footwear, efforts to sanitize footwear prior to an individual entering an establishment or residence have been undertaken. In many cases, these efforts have resulted in large stationary devices that require the user to remove their footwear and place the footwear inside the device for a period of time. Sanitation is done by exposing the contaminants to ultraviolet light. The ultraviolet light disrupts the DNA of the biological contaminants making them unable to perform vital cellular functions. To power the ultraviolet lights, these devices require a connection to an external power source; making placement of the device accessibility to potential user's a concern. Alternative devices may use a battery to generate the power required for sanitation. Batteries, however will run out of charge, need to be replaced after time and cause excess waste.

As a result of size limitations, lack of user-friendliness and disposing of batteries that are harmful to the environment, these devices have not been incorporated into the everyday use of the walking/footwear routine. Therefore, it is a primary object of the invention to provide a portable self-powering sanitizing device that has an internal power generator that can sanitize footwear and reduce waste.

The present invention relates to a self-powered, footwear sanitizing system, configured to substantially neutralize biological contaminants on the soles, hooves, paws, or any object. When a wearer of shoes steps on or someone places an object onto the system, the system has a mat configured to support a wearer of shoes that steps onto the mat or an object placed on it. The system has a means for delivering the sanitizing radiation to the mat and to the underside of the wearer's shoes and a generator configured to power the delivering means when a wearer steps onto the mat.

DETAILED DESCRIPTION OF THE INVENTION

The primary embodiment is represented by the drawings on pages 1 and 2. Drawings (FIGS. 1, 2, 3), FIG. 1 is a top view of the invention showing the orientation of the individual LED/power modules arranged in a grid-like structure (line 1). This structure is bordered by the sidewalls (line 2) which is made up of an opaque polyvinyl material. The sidewall provides a barrier to the UVC light that is scattered toward the side of the mat.

FIG. 2 is a perspective view of the two sides of the primary embodiment. The height of the sidewall (line 3) can range from 10 to 20 millimeters. The length and width dimensions can easily change and we expect that the market will dictate the optimum sizes of the embodiment.

FIG. 3 displays a cross section of the side view of the primary embodiment of the invention. Each mat would consist of the sidewalls (line 10), a top layer (line 4) which serves to hold the LED/power module in place and is transparent to UVC light to allow the UVC light to shine on the footwear sole. Below this is a UVC LED (line 5) that is connected by electrical leads to the piezo-electrical generator module (line 8). When a person steps upon or places an object on the module, it deforms the crystal structure of the piezo-electric material and generates a voltage to the UVC LED. Below the LED is a reflecting layer (line 6) to redirect the internally scattered UVC light upwards to the footwear soles or objects. Beneath this is an insulating layer (line 7). Lines 9 and 10 correspond to the sidewall and bottom layers and is made of an UVC opaque polyvinyl material. Line 11 points to the electrical connections from the power generating module to the LEDs.

FIG. 4 on page 3 of the drawings shows a top view of the Variations A and B of the mechano-luminescence mat. (Line 12) points to a sidewall of UVC opaque polyvinyl material. (Line 13) points to the grid lines cut into the mechanoluminescence layers of the two variations.

FIG. 5 is a perspective view of the mat. (line 14) points to the sidewall of the mat.

The external appearances between the primary specifications and the variations embodiments are very similar. The grid lines cuts proposed in the polyvinyl fluoridene and vinyl surface layers give a visual appearance that is similar to the LED, power generator/power storage modules of FIGS. 1 & 2. In the primary specification embodiment and the variations A and B embodiments, it is the feature that limits the amount of UVC that is released into the environment. This is the basis for Claim 2.

Variation # A This embodiment has a polyvinyl fluoridene (PVFD) layer FIG. 6, line 17 which is a mechano-luminescent material. When a wearer of shoes steps onto the mat or an object is placed on the mat, the deformation of the PVFD layer 17 emits a white light in the visual range. This white light excites the white light to UVC up-converting phosphor layer 16 to emit UVC at the 254 nm range thereby sanitizing the footwear, or object. This ability to self-power the UVC sanitizing system for both the primary and Variations A & B embodiments provides the basis for Claim 1. Layer 18 is an aluminized polyvinyl material that acts as a reflecting layer for any white light or UVC scattered light within the mat to be reflected to the footwear sole.

Variation # B. This proposed variation of these embodiments differs only from Variation # A in that layers lines 15 and 16 of Variation #A, FIG. 6, are combined together by the doping of the PVFD with the up-converting phosphor to become the one layer line 23, FIG. 7. All of the other layers in FIG. 7 correspond to their counterparts in Variation #A, FIG. 6. Layer line 22, FIG. 7 is the UVC transparent polyvinyl top layer, line 24 is the aluminized reflecting layer. Layer line 25 is the base layer, sidewall line 26 and cut grid-lines 27.

A worker practiced in the art would recognize that all the embodiments of the self-powered footwear sanitizing system share the advantage of having the UVC generating source within several millimeters of the footwear sole or object. This significantly lowers the power requirements to generate the UVC, as well as, lowering the duration of the exposure time to achieve maximum sanitizing. Most systems available of UVC sanitizing footwear designs have the UVC source much further away from the footwear requiring more power and longer duration exposure times. All of the embodiments provide the user of the footwear sanitizing systems to fine tune the level of sanitation by the amount of steps the user takes on the mat. Multiple steps increases the exposure time of the UVC treatment feature. Since it is only the areas directly under the soles of the footwear that emit the UVC light; the soles shield the UVC from being scattered and released into the environment. This is the basis for Claim 2.

BRIEF SUMMARY OF THE INVENTION

The brief summary of the embodiments of the invention will be made below with reference to the accompanying figures, wherein like numerals represent corresponding parts of the Figures.

Figure 1:
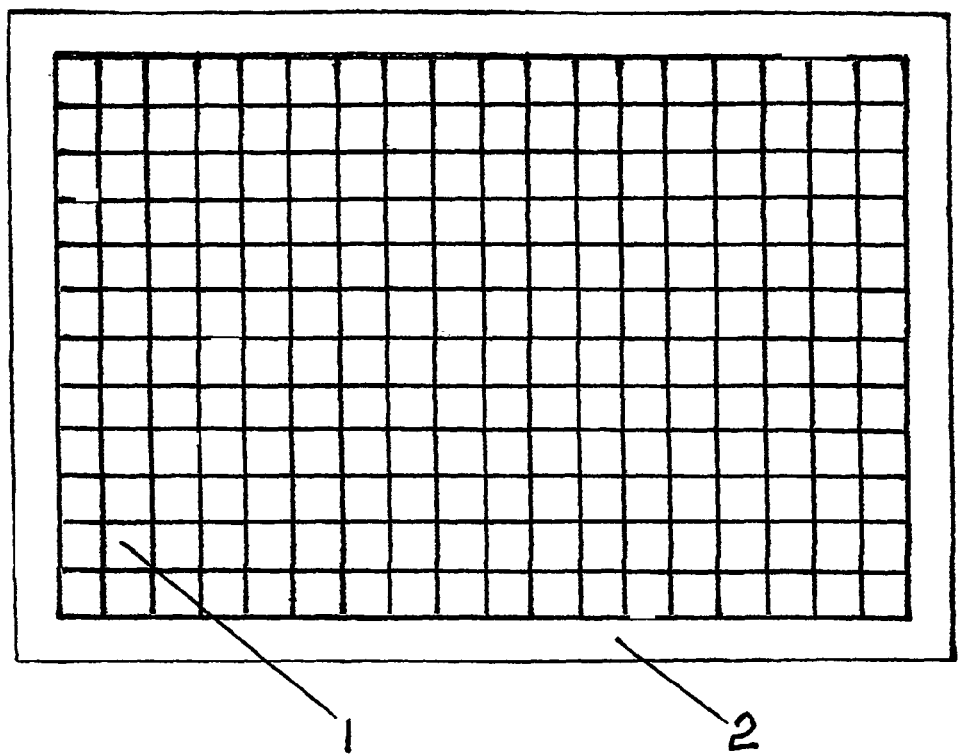
FIG. 1 Is a top view of one of the primary embodiments looking down onto the mat, showing the grid-like orientation of the modules 1, comprising the mat and border 2.
Figure 2:
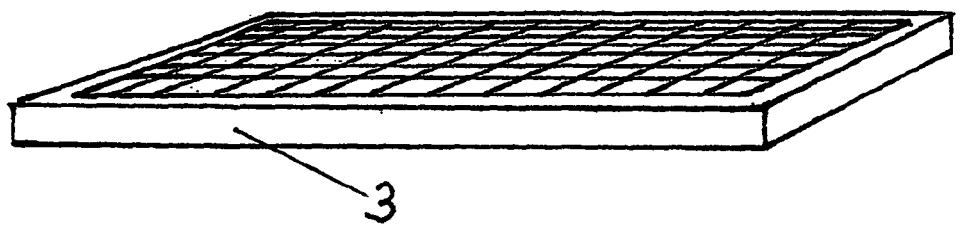
FIG. 2 Is a perspective view of one of the sides of the mat showing a side wall 3 and approximate thickness of the mat.
Figure 3:
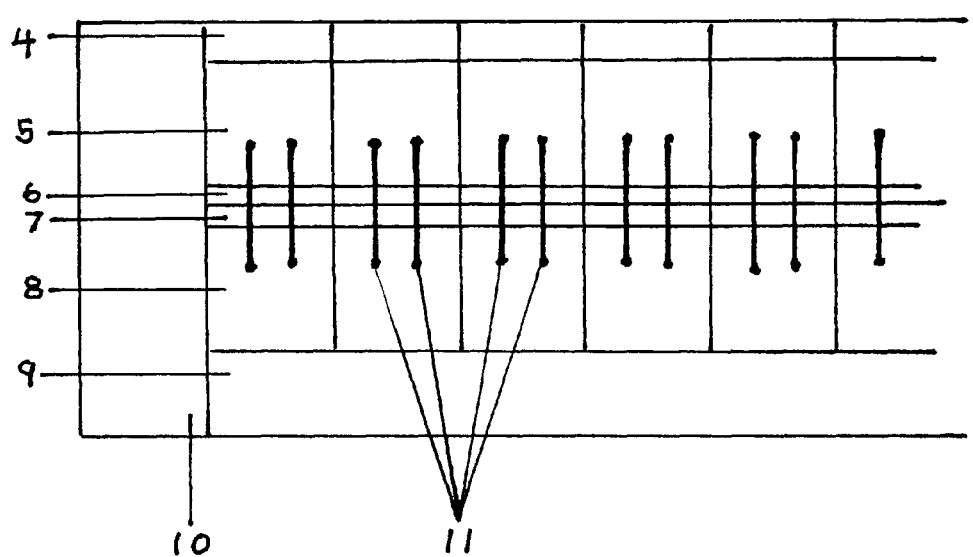

FIG. 3 Is a schematic representation of a cross-sectional view of a portion of the mat showing a UVC transparent polyvinyl top layer 4, a UVC LED module 5, connected electrically by positive and negative electrodes 11, to a piezo-electric generator and capacitance module 8, the layer below the LED module 5, is a reflecting layer 6, of aluminized foil, below this is an electrically insulating layer 7, below this layer is a piezoelectric generator and capacitance storage module 8, the bottom layer 9, is a layer of UVC opaque polyvinyl substrate of the same materials as the side wall 10 and top border 2

Figure 4:
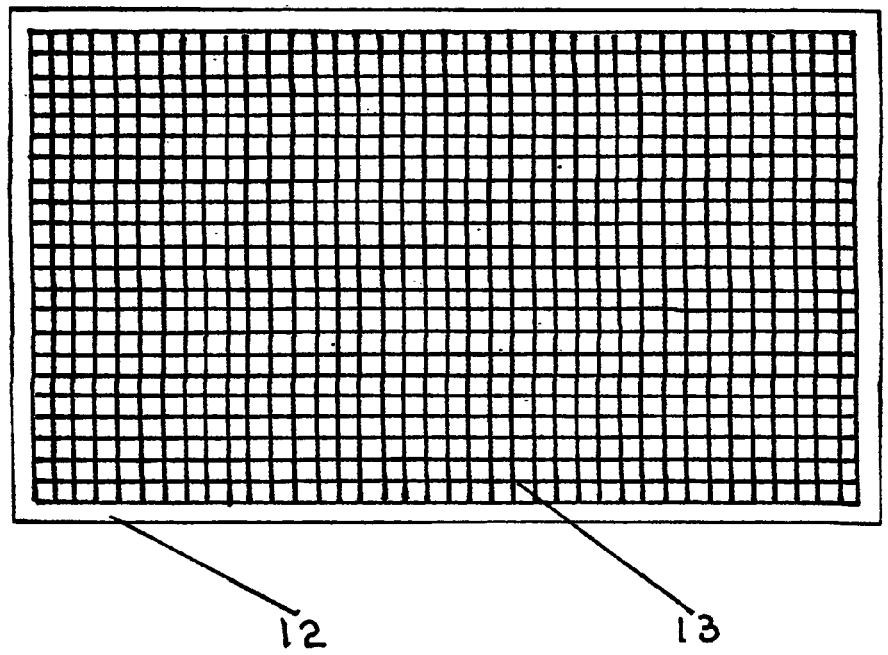
Figure 6:
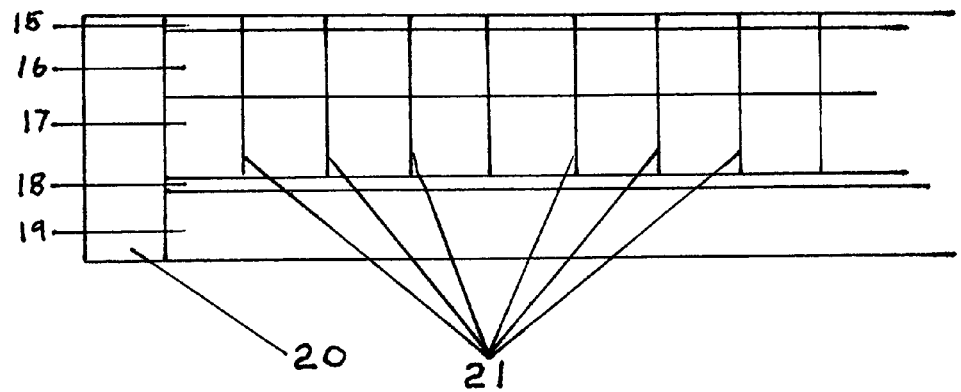

FIG. 4 Depicts a top view of the mat in the embodiments of the 2 Variations (A & B), showing the grid lines 13, cut into the layers 15, 16, 17, of FIG. 6.

Figure 5:
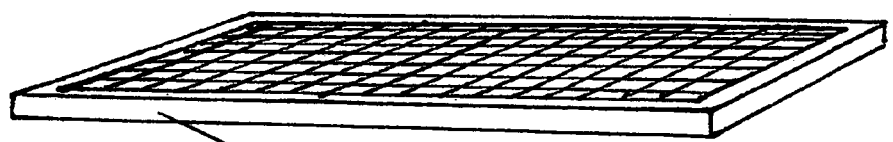

FIG. 5 Depicts a perspective view of two of the four similar side views of the FIG. 4.

FIG. 6 Depicts a portion of a side view cross section of the mat (Variation # A) showing a top layer 15 of UVC transparent polyvinyl, which lies on top of the phosphor layer 16, which is above the PVFD layer 17, with an aluminized reflecting layer 18, between it and the bottom backing layer 19, with side wall 20, and cut grid lines 21, in layers 15, 16, and 17.

Figure 7:
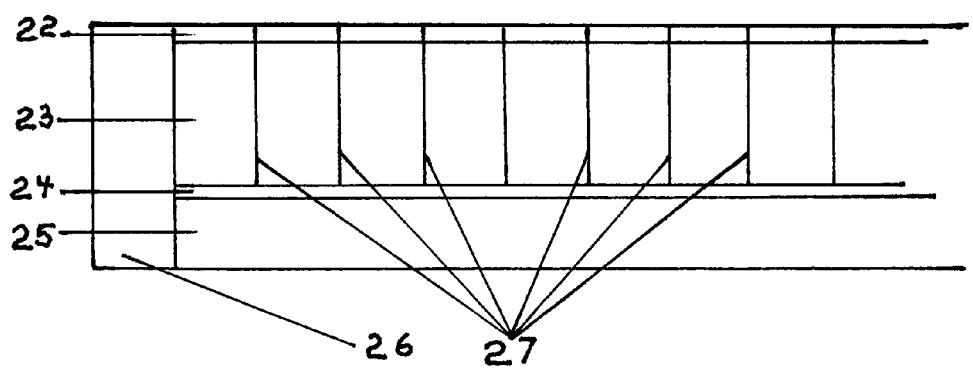

FIG. 7 Depicts a cross sectional side view of a portion of the mat (Variation # B) which has a polyvinyl UVC transparent top layer 22, above layer 23, of the PVFD doped with a white light to UVC up-converting phosphor. Below this layer is an aluminized reflecting layer 24, above the UVC opaque backing layer 25, the side wall 26, is made of the same material as layer 25, with the grid lines 27 cut into polyvinyl fluoridene doped with UVC phosphor in layer 22 and top layer 23.

In these embodiments, the system comprises a mat. The mat is configured to support the wearer of shoes that steps onto the system. The mat comprises a flexible material. The mat comprises a polyvinyl substrate. The mat comprises an ultraviolet (254 nm) radiation generating substrate and a transparent polyvinyl substrate. The mat is comprised of a thickness range of 10 millimeters to 20 millimeters.

In these embodiments, the system comprises a means for delivering a sanitizing radiation. The means for delivering the sanitizing radiation is configured to emit radiation that substantially disrupts the cellular function of biological contaminants. In some embodiments, the means for delivering the sanitizing radiation comprises a radiation emitting light source. In these embodiments the radiation emitting light source comprises a light emitting diode or a white light mechano-luminescence PVFD. In some embodiments, the material is PVFD with an up-converting white light to UVC phosphor layer. In other embodiments, the phosphor or other up-converting white light to UVC dopant or ligand and PVFD are mixed together.

In these embodiments, the means for delivering the sanitizing material is configured to emit ultraviolet electromagnetic radiation Subtype C, at a wavelength of 254 nm. In these embodiments, the means for delivering the sanitizing radiation is configured to emit a radiation wavelength of 100 nanometers to 400 nanometers. In some embodiments, the means for delivering the sanitizing radiation is configured to receive an input voltage range of 1 volt direct current to 12 volts direct current. In these embodiments, the means for delivering the sanitizing radiation is configured to have an output power of 300 milliwatts at 700 milliamps. In some embodiments, the self-powering generator is configured to pulse for a time range of 0.1 to 10 seconds.

In these embodiments, the system is comprised of a generator. The generator is configured to provide power to the means for the delivering the sanitizing radiation. The generator output is configured to be connected to a capacitor. The generated voltage is configured to power the UVC LED's. In some embodiments, the self-powering generator is configured to provide power by piezo-electricity or mechano-luminescence. In these embodiments, the self-powering generator is configured to polarize in the presence of an external stress. The self-powering generator is comprised of piezo-electric ceramics, or polymers. The piezo-electric ceramic is selected from a group consisting of barium titanate, lead titanate, lead zirconate, potassium niobate, lithium niobate, lithium titanate, sodium tungstate, zinc oxide, Ba2NaNb5O5, Pb2KNb5O15, sodium potassium niobate, bismuth ferrite, sodium niobate, bismuth titanate and sodium bismuth titanate. In some embodiments, the self-powering generator comprises piezo-electric crystals. In alternative embodiments, the piezo-electric crystals are selected from a group of quartz, ammonium dihydrogen phosphate, lithium sulfate, antimony sulfoidide, berlinite sucrose, Rochelle salt, topaz and tourmaline-group minerals. In some embodiments, the self-powering generator comprises a polymer. The polymer is comprised of polyvinyl fluoridene which generates light in the visual range. In some embodiments, a polymer generates white light which is up-converted by a phosphor such as Lu706F9;Pr3f, or other white light to UVC up-converting materials.

In certain embodiments, the system comprises an insulation layer. The insulation layer is configured to electrically isolate the generator from the LED to keep it from short circuiting. In these embodiments, the insulation layer comprises a dilectric material. The insulation layer comprises a polyvinyl substrate.

In certain embodiments, the sanitizing mat comprises a light reflecting layer. The light reflecting layer is configured to reflect extraneous light produced by the light emitting diodes back to the footwear soles. In some embodiments, the light reflecting layer is configured to have a reflective surface. The light reflecting layer may be comprised of aluminum film or polyvinyl tetra-fluoride (PVTF) or other reflective materials.

The systems are configured in a layered format. In these embodiments, the layered format is configured to have the mat, the means for delivering the sanitizing radiation, generator, insulation layer and light reflecting layer in a flat surface that a user can step on. In this embodiment, the system is configured to have the means for delivering the sanitizing material as the second layer, the light reflecting layer affixed to the top side of the floor backing layer of the mat encasing the aforementioned layers.

Design variations from the original Provisional Application (filed on May 2, 2014).

A In certain embodiments, the system is configured with a layer of polyvinyl UVC transparent substrate. Under the substrate is the phosphor layer of Lu706Fp;Pr3+ or similar UVC up-converting phosphor. This layer converts the white light generated by the PVFD layer into 254 nm UVC light. Under this phosphor layer is the PVFD (polyvinyl fluoridene) layer and this layer is backed by aluminum foil or aluminized Mylar layer that reflects scattered UVC and white light to the sole of the footwear. Beneath this layer of reflective substrate is the floor layer of the system.

B In certain embodiments, the system may be configured with a layer of polyvinyl UVC transparent substrate. Under this substrate layer is a layer of PVFD with a dopant/ligand or mixture of polymer PVFD and phosphors that generates the sanitizing UVC (254 nm) light. The last layers are the floor layers of the system, as per Variation # A.

Persons of ordinary skill in the art may appreciate that numerous design configurations may be possible to enjoy the functional benefits of the inventive systems. Also a person of ordinary skill in the art can readily appreciate that these mats can also sanitize feet, hooves, and paws of animals or objects. Thus given the wide variety of configurations and arrangements of the embodiments of the present invention and the scope of the invention, is reflected by the breadth of the claims below rather than narrowed by the embodiments described above.

What is claimed:

1. A self-powered footwear sanitizing system configured to substantially neutralize biological contaminants on the soles of shoes when a wearer of shoes steps onto the system, the system comprising; a mat configured to support a wearer of shoes that steps onto the mat that shines UVC light therein; a means for delivering the sanitizing UVC light from the mat to the underside of the wearer's shoes, and a piezo-electric powered LED's and mechano-luminescence UVC generator configured to power the delivering means when the wearer steps onto the mat.

2. The device of claim 1, wherein the grid-like structure of the embodiments of the mat allows only the section under the foot to generate the sanitizing UVC light, thereby allowing the footwear to act as a barrier to shield most of the UVC light from radiating into the environment.

* * * * *